(12) United States Patent
Cao et al.

(10) Patent No.: US 8,163,259 B2
(45) Date of Patent: Apr. 24, 2012

(54) INTERGROWN MOLECULAR SIEVE, ITS SYNTHESIS AND ITS USE IN THE CONVERSION OF OXYGENATES TO OLEFINS

(75) Inventors: Guang Cao, Branchburg, NJ (US); Matu J. Shah, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/009,518

(22) Filed: Jan. 19, 2011

(65) Prior Publication Data

US 2011/0112350 A1 May 12, 2011

Related U.S. Application Data

(62) Division of application No. 11/788,327, filed on Apr. 19, 2007, now Pat. No. 7,906,099.

(60) Provisional application No. 60/812,412, filed on Jun. 9, 2006.

(51) Int. Cl.
*C07C 1/24* (2006.01)
*C01B 37/08* (2006.01)

(52) U.S. Cl. ........ 423/305; 423/702; 423/718; 423/700; 423/DIG. 30; 585/640

(58) Field of Classification Search .................. 423/700, 423/702, 718, 305, DIG. 30; 585/640
See application file for complete search history.

(56) References Cited

U.S. PATENT DOCUMENTS

| 5,370,851 | A | 12/1994 | Wilson |
| 6,334,994 | B1 | 1/2002 | Wendelbo et al. |
| 6,906,233 | B2 | 6/2005 | Mees et al. |
| 6,936,566 | B2 | 8/2005 | Mees et al. |
| 6,989,470 | B2 | 1/2006 | Wang |
| 7,247,287 | B2 | 7/2007 | Cao et al. |
| 2004/0116762 | A1* | 6/2004 | Mees et al. ............ 585/640 |
| 2004/0253163 | A1* | 12/2004 | Cao et al. ............. 423/305 |

FOREIGN PATENT DOCUMENTS

WO    WO 02/070407    9/2002

OTHER PUBLICATIONS

Wilson et al., "*Synthesis, characterization and structure of SAPO-56, a member of the ABC double-six-ring family of materials with stacking sequence AABBCCBB*," Microporous and Mesoporous Materials, vol. 28 (1999), pp. 125-137.

Breck, "*Theoretical Zeolite Structures*," Zeolite Molecular Sieves; Structure, Chemistry, and Use (1984), p. 47.

* cited by examiner

*Primary Examiner* — David M Brunsman
(74) *Attorney, Agent, or Firm* — Darryl M. Tyus; Xiaobing Feng (57) ABSTRACT

A molecular sieve comprises at least one intergrown phase of an AFX framework-type molecular sieve and a CHA framework-type molecular sieve and is conveniently synthesized using a combination of N,N,N'N'-tetramethylhexane-1,6-diamine and N,N-dimethylcyclohexylamine as organic directing agents.

18 Claims, 4 Drawing Sheets

Figure 1.

Figure 2. Indexing of XRD Patterns

Figure 3. Effect of Template Ratio

Figure 4

INTERGROWN MOLECULAR SIEVE, ITS SYNTHESIS AND ITS USE IN THE CONVERSION OF OXYGENATES TO OLEFINS

PRIORITY CLAIM

This application is a divisional of and claims priority to U.S. patent application Ser. No. 11/788,327, filed Apr. 19, 2007, now U.S. Pat. No. 7,906,099, and U.S. Provisional Application No. 60/812,412, filed Jun. 9, 2006, the disclosures of which is are herein incorporated by reference in their entireties.

FIELD OF THE INVENTION

This invention relates to an intergrown molecular sieve, its synthesis and its use in the conversion of oxygenates to olefins.

BACKGROUND OF THE INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA framework type, such as SAPO-34.

Regular crystalline molecular sieves, such as the CHA framework-type materials, are built from structurally invariant building units, called Periodic Building Units, and are periodically ordered in three dimensions. Disordered structures showing periodic ordering in less than three dimensions are, however, also known. One such disordered structure is a disordered planar intergrowth in which the building units from more than one framework type are present. Such intergrowths frequently have significantly different catalytic properties from their end members.

For example, the zeolite ZSM-34 is a well known intergrowth of ERI and OFF framework-type molecular sieves and exhibits an MTO performance far superior to its individual component materials. More recently, silicoaluminophosphate molecular sieves comprising at least one intergrown phase of an AEI framework-type material and a CHA framework-type material have been synthesized and have been found to be particularly attractive catalysts for oxygenate-to-olefin reactions.

For example, U.S. Pat. No. 6,334,994 discloses a silicoaluminophosphate molecular sieve, referred to as RUW-19, which is said to be an AEI/CHA mixed-phase composition. In particular, RUW-19 is reported as having peaks characteristic of both AEI and CHA framework-type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. RUW-19 is reported to be active as a catalyst in the production of light olefins from methanol (MTO).

In addition, International Patent Publication No. WO 02/70407, published Sep. 12, 2002, discloses a silicoaluminophosphate molecular sieve, now designated EMM-2, comprising at least one intergrown form of molecular sieves having AEI and CHA framework types, wherein said intergrown form has an AEI/CHA ratio of from about 5/95 to 40/60 as determined by DIFFaX analysis, using the powder X-ray diffraction pattern of a calcined sample of said silicoaluminophosphate molecular sieve. EMM-2 has been found to exhibit significant activity and selectivity as a catalyst for the production of light olefins from methanol (MTO).

The Periodic Building Unit for both AEI and CHA framework-type molecular sieves is the double six-ring layer. A number of other molecular sieves are known to have the same or similar double six-ring layer as their building unit, including AFX framework-type materials. According to the present invention, a new intergrown material of the AFX and CHA framework-type molecular sieves has been synthesized and has been found to exhibit activity as a catalyst in the conversion of oxygenates to olefins.

U.S. Pat. No. 5,370,851 describes the synthesis of SAPO-56, a silicoaluminophosphate of the AFX framework type, using N,N,N'N'-tetramethylhexane-1,6-diamine as a directing agent. According to the '851 patent, SAPO-56 is useful as a catalyst in a large variety of hydrocarbon conversion processes, such as cracking, hydrocracking, alkylation of both aromatics and isoparaffins, isomerization, polymerization, reforming, hydrogenation, dehydrogenation, transalkylation, dealkylation, hydration, dehydration, hydrotreating, hydrodenitrogenation, hydrodesulfurization, methanation and the syngas shift process.

U.S. Published Patent Application No. 2004/0253163, published Dec. 16, 2004, discloses the synthesis of a silicoaluminophosphate molecular sieve having the CHA framework type employing a directing agent of the formula:

$R^1R^2N-R^3$ wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally, substituted by 1 to 3 alkyl groups having from 1 to 3 carbon atoms; and 4- to 8-membered heterocyclic groups having from 1 to 3 heteroatoms, said heterocyclic groups being, optionally, substituted by 1 to 3 alkyl groups having from 1 to 3 carbon atoms and the heteroatoms in said heterocyclic groups being selected from the group consisting of O, N, and S. Preferably, the directing agent is selected from N,N-dimethylcyclohexylamine, N,N-dimethylmethyl-cyclohexylamine, N,N-dimethylcyclopentylamine, N,N-dimethylmethyl-cyclopentylamine, N,N-dimethylcycloheptylamine, N,N-dimethylmethylcycloheptylamine, and most preferably is N,N-dimethylcyclohexylamine.

SUMMARY OF THE INVENTION

In one aspect, the invention resides in a molecular sieve comprising at least one intergrown phase of an AFX framework-type molecular sieve and a CHA framework-type molecular sieve.

Preferably, said molecular sieve is a silicoaluminophosphate or an aluminophosphate.

In one embodiment, the molecular sieve has an X-ray diffraction pattern including at least the following reflection peaks:

2θ (CuKα)
9.50 (±0.05)
12.91 (±0.05)
13.96 (±0.05)
16.02 (±0.05)
17.72 (±0.05)
20.62 (±0.05)
21.98 (±0.05)
22.44 (±0.05)
23.10 (±0.05)
24.86 (±0.05)
25.96 (±0.05)

In a further aspect, the invention resides in a method of synthesizing a molecular sieve comprising at least one intergrown phase of an AFX framework-type molecular sieve and a CHA framework-type molecular sieve, the method comprising:

(a) preparing a reaction mixture comprising sources of alumina, phosphorus, and, optionally, silica and further comprising at least one first organic directing agent for directing the synthesis of an AFX framework-type molecular sieve and at least one second organic directing agent for directing the synthesis of a CHA framework-type molecular sieve;

(b) maintaining said reaction mixture under conditions sufficient to form crystals of said molecular sieve; and (c) recovering said molecular sieve.

In one embodiment, said at least one first organic directing agent comprises N,N,N'N'-tetramethylhexane-1,6-diamine and said at least one second organic directing agent comprises N,N-dimethylcyclohexylamine.

Preferably, said mixture in (a) has a silica to alumina molar ratio of at least 0.3.

In a further aspect, the invention resides in a process for producing olefins comprising contacting an organic oxygenate compound under oxygenate conversion conditions with a catalyst comprising a silicoaluminophosphate molecular sieve comprising at least one intergrown phase of an AFX framework-type molecular sieve and a CHA framework-type molecular sieve.

DETAILED DESCRIPTION OF THE INVENTION

The present invention relates to a silicoaluminophosphate or aluminophosphate molecular sieve comprising at least one intergrown phase of an AFX framework-type and a CHA framework type, to the synthesis of this novel intergrowth and to its use in a process for the conversion of oxygenates, particularly methanol, to olefins, particularly ethylene and propylene.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e., in two, one, or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

Figure 4:
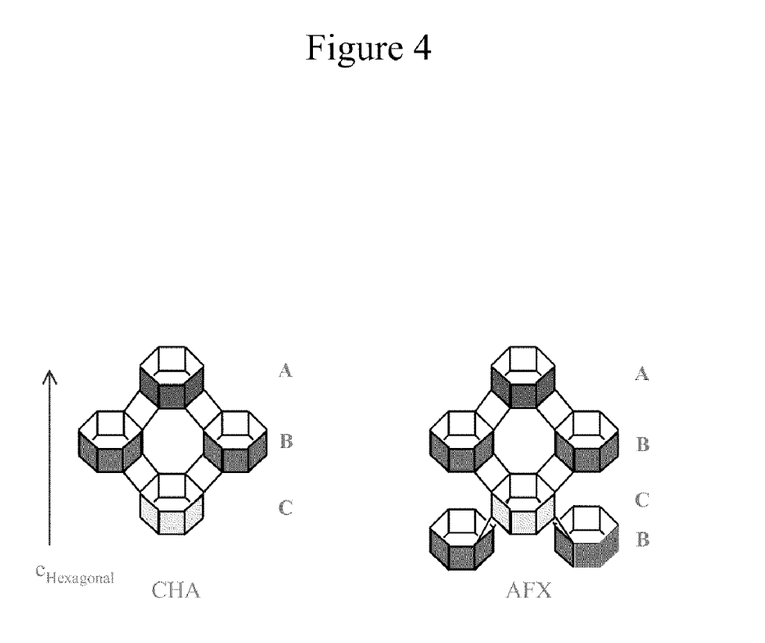
FIG. 4 illustrates the hexagonal building units of AFX and CHA framework-type molecular sieves

The molecular sieves described herein can be disordered planar intergrowths of end-member structures AFX and CHA. Both of these two framework types belong to the group that have double 6-ring (D6R) as secondary building unit (group 4 according to D. W. Breck, Zeolite Molecular Sieves, Structure, Chemistry, and Use, 1984, p. 47). The AFX structure is built from hexagonal stacking of D6Rs in ABCB sequence via tilted 4-ring linkages, whereas the CHA structure is similarly constructed, except that the D6R stacking is in ABC sequence. FIG. 4 illustrates this relationship.

This structural similarity supports the current finding that, via proper synthesis manipulation, it may be possible to make the AFX and CHA frameworks intergrow into each other, affording novel microporous materials. The intergrown phases may, for example, have the following D6R stacking sequence:

In the above case, the ABCB sequence (an AFX layer) inserts itself into the structure of CHA along the hexagonal axis (the crystal structure of AFX is of hexagonal symmetry and that of SAPO-34 is of rhombohedral symmetry). The consequence of such an intergrowth is that the translational periodicity along the c axis (the hexagonal axis) is disrupted and therefore all CHA diffraction lines with Miller indices (hk0) should remain sharp while most others should become broadened. The coexistence of broad and sharp peaks is a major indicator of intergrowths and, as will be apparent from the Examples, is present in the intergrowths of the invention.

In particular, the present AFX-CHA intergrowth exhibits in its as-synthesized form an X-ray diffraction pattern including at least the following reflection peaks:

2θ (CuKα)
9.50 (±0.05)
12.91 (±0.05)
13.96 (±0.05)
16.02 (±0.05)
17.72 (±0.05)
20.62 (±0.05)
21.98 (±0.05)
22.44 (±0.05)
23.10 (±0.05)
24.86 (±0.05)
25.96 (±0.05)

The X-ray diffraction data referred to herein are collected with a Siemens D500 diffractometer, using copper K-alpha radiation. The diffraction data are recorded by step-scanning at 0.02 degrees of two-theta, where theta is the Bragg angle, and a counting time of 1 second for each step.

The materials of the present invention usually have broad features at 12.91±0.05, 17.72±0.05, 21.98±0.05, 22.44±0.05, and 25.99±0.05 degrees 2θ, each broad feature being characteristic of the AFX/CHA intergrown phase.

In one embodiment, the AFX/CHA intergrowth can have from about 1% to about 99% of the AFX crystal structure, for example from about 5% to about 95%, alternately from about 10% to about 90% or from about 20% to about 80%. Similarly, the AFX/CHA intergrowth can have from about 1% to about 99% of the CHA crystal structure, for example from about 5% to about 95%, alternately from about 10% to about 90% or from about 20% to about 80%. The relative proportions of each of the phases can be analyzed by X-ray diffraction and, in particular, by comparing the observed patterns with calculated patterns generated using algorithms to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for randomly intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA, and KFI, as reported by K. P. Lillerud et al. in "Studies in Surface Science and Catalysis", 1994, Vol. 84, pp. 543-550.

Where the materials of the invention are silicoaluminophosphates, they typically have a silica to alumina molar ratio (Si/Al$_2$) from about 0.10 to about 0.60, preferably from about 0.15 to about 0.50.

The intergrown molecular sieve of the present invention may conveniently be prepared by a method that comprises the steps of:

(a) preparing a reaction mixture comprising sources of alumina, phosphorus, and, optionally, silica and further comprising at least one first organic directing agent for directing the synthesis of an AFX framework-type molecular sieve and at least one second organic directing agent for directing the synthesis of a CHA framework-type molecular sieve;

(b) maintaining said reaction mixture under conditions sufficient to form crystals of said molecular sieve; and (d) recovering said molecular sieve.

Typically, the reaction mixture has a silica to alumina molar ratio (SiO$_2$/Al$_2$O$_3$) of at least 0.1, since with some syntheses when SiO$_2$/Al$_2$O$_3$ is less than 0.2, SAPO-17 forms rather than the desired CHA/AFX intergrowth. More specifically, the reaction mixture preferably has a molar composition within the following ranges:

P$_2$O$_5$:Al$_2$O$_3$ from about 0.75 to about 1.25,
SiO$_2$:Al$_2$O$_3$ from 0.1 to about 0.8, and
H$_2$O:Al$_2$O$_3$ from about 25 to about 80.

The crystallization step (b) is generally conducted at a temperature between about 120° C. and about 220° C., typically between about 140° C. and about 200° C., for a period of time of from about 12 to 480 hours, typically about 24 to 360 hours. In particular, it is found that production of the desired CHA/AFX intergrowth is facilitated by conducting the crystallization in at least two stages including a first stage at a first temperature, typically in the range of about 150° C. to about 200° C., for a first period of time, typically from about 24 to about 360 hours, and a second stage at a second temperature higher than the first temperature, typically in the range of about 170° C. to about 220° C., for a second period of time, typically from about 24 to about 96 hours. The reaction mixture may be agitated during one or both the crystallization stages, but more preferably is agitated during the first stage and held static during the second stage.

Any organic directing agent capable of directing the synthesis of an AFX framework-type molecular sieve can be used as the first organic directing agent, but preferably the first organic directing agent is N,N,N',N'-tetramethyl-1,6-hexanediamine (TMHDA).

Similarly, any organic directing agent capable of directing the synthesis of a CHA framework-type molecular sieve can be used as the second organic directing agent. For example, suitable organic directing agents for directing the synthesis of CHA framework-type materials include adamantammonium compounds, such as N,N,N-trimethyl-1-adamantammonium compounds, N,N,N-trimethyl-2-adamantammonium compounds, and N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in: (1) *Zeolites and Related Microporous Materials*: State of the Art 1994, Studies of Surface Science and Catalysis, Vol. 84, pp. 29-36; (2) *Novel Materials in Heterogeneous Catalysis* (ed. Terry K. Baker & Larry L. Murrell), Chapter 2, pp. 14-24, May 1990; (3) J. Am. Chem. Soc., Vol. 122, pp. 263-273, 2000; and (4) U.S. Pat. Nos. 4,544,538 and 6,709,644.

More preferably, the second organic directing agent is a compound having the formula:

$R^1R^2N—R^3$ wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally, substituted by 1 to 3 alkyl groups having from 1 to 3 carbon atoms; and 4- to 8-membered heterocyclic groups having from 1 to 3 heteroatoms, said heterocyclic groups being, optionally, substituted by 1 to 3 alkyl groups having from 1 to 3 carbon atoms and the heteroatoms in said heterocyclic groups being selected from the group consisting of O, N, and S. Preferably, the directing agent is selected from N,N-dimethylcyclohexylamine, N,N-dimethylmethyl-cyclohexylamine, N,N-dimethylcyclopentylamine, N,N-dimethylmethyl-cyclopentylamine, N,N-dimethylcycloheptylamine, N,N-dimethylmethylcycloheptylamine, and most preferably is N,N-dimethylcyclohexylamine (DMCHA).

The amount of the first organic structure directing agent is typically such that the ratio of the first directing agent to alumina is from about 0.1 to about 2.0, whereas the amount of the second organic structure directing agent is typically such that the ratio of the second directing agent to alumina is from about 0.1 to about 2.0.

Examples of suitable aluminum sources for use in the above reaction mixture include hydrated aluminum oxides such as boehmite and pseudoboehmite. The reactive source of phosphorus used in the mixture is conveniently phosphoric acid. The reactive source of silicon used in the above mixture may be a silicate, e.g., fumed silica, such as Aerosil (available from Degussa) or Cabosil (available from Cabot), a tetraalkyl orthosilicate, or an aqueous colloidal suspension of silica, for example, that sold by E.I. du Pont de Nemours under the tradename Ludox.

Synthesis of the new intergrowth may be facilitated by the presence of at least 0.1 ppm, such as at least 10 ppm, for example, at least 100 ppm, conveniently at least 500 ppm of seed crystals based on total weight of the reaction mixture. The seed crystals can be homostructural with the crystalline material of the present invention, for example, the product of a previous synthesis, or can be a heterostructural crystalline material.

Typically, the crystalline product is formed in solution and can be recovered by standard means, such as by centrifugation or filtration. The separated product can also be washed, recovered by centrifugation or filtration, and dried.

As a result of the crystallization process, the recovered crystalline product contains within its pores at least a portion of the organic directing agents used in the synthesis. In a preferred embodiment, activation is performed in such a manner that the organic directing agents are removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agents from the intracrystalline pore system.

Once the intergrowth crystalline material of the invention has been synthesized, it can be formulated into a catalyst composition by combination with other materials, such as binders and/or matrix materials, which provide additional hardness or catalytic activity to the finished catalyst.

In one embodiment, in addition to a first AFX/CHA intergrowth crystalline material according to the invention, the molecular sieve composition can comprise a second type of molecular sieve. This second molecular sieve can itself be an intergrowth (e.g., another AFX/CHA intergrowth crystalline material) or a single crystalline phase material (e.g., a CHA molecular sieve material, an AFX molecular sieve material, or the like, or a combination thereof), or a mixture thereof. In such embodiments, the first intergrowth material can be present in the molecular sieve composition in an amount from about 1% to about 99% by weight, for example from about 5% to about 95% by weight, alternately from about 10% to about 90% by weight or from about 20% to about 80% by weight. In this embodiment, the second type of molecular sieve can be present in the molecular sieve composition in an amount from about 99% to about 1% by weight, for example from about 95% to about 5% by weight, alternately from about 90% to about 10% by weight or from about 80% to about 20% by weight. The relative proportions of each of the materials in the molecular sieve compositions of these embodiments can be determined by known techniques including, but not limited to, x-ray diffraction (XRD) peak comparisons, e.g., using software packages such as DIFFaX or the like.

Materials which can be blended with the intergrown crystalline material (and/or molecular sieve composition) of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product can range from 10 to 90 weight percent of the total catalyst, preferably 20 to 80 weight percent of the total catalyst.

The intergrown crystalline material (and/or molecular sieve composition) of the invention can be used to dry gases and liquids; for selective molecular separation based on size and polar properties; as an ion-exchanger; as a chemical carrier; in gas chromatography; and as a catalyst in organic conversion reactions. Examples of suitable catalytic uses include: (a) hydrocracking of heavy petroleum residual feedstocks, cyclic stocks and other hydrocrackate charge stocks, normally in the presence of a hydrogenation component selected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes; (j) catalytic reduction of nitrogen oxides; and (k) synthesis of monoalkylamines and dialkylamines.

In particular, however, the intergrown crystalline material (and/or molecular sieve composition) of the invention is useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen, and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally, with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about $0.01\ hr^{-1}$ to about $500\ hr^{-1}$, such as in the range of from about $0.5\ hr^{-1}$ to about $300\ hr^{-1}$, for example, in the range of from about $0.1\ hr^{-1}$ to about $200\ hr^{-1}$.

A practical embodiment of a reactor system for the oxygenate conversion process is a circulating fluid-bed reactor with continuous regeneration, similar to a modern fluid catalytic cracker. Fixed beds are generally not preferred for the process because oxygenate-to-olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$-$C_4$ aldehyde composition and/or a $C_4$-$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example, at least 50° C., higher than the temperature used for the oxygenate reaction zone and is arranged to produce at least 0.1 wt %, such as at least 1 wt %, for example, at least about 5 wt % of the integrated hydrocarbon co-catalyst, based on total weight of the molecular sieve. Such preliminary treating to increase the carbon content of the molecular sieve is known as "pre-pooling" and is further described in U.S. Patent Application Publication Nos. 2005/0101815, 2005/0101816 and 2005/0101817, all of which were published on May 12, 2005, and are fully incorporated herein by reference.

The invention will now be more particularly described with reference to the following Examples. In the Examples, X-ray Powder Diffractograms were recorded on Siemens D500 diffractometer with voltage of 40 kV and current of 30 mA, using a Cu target and Ni-filter ($\lambda$=0.154 nm). Elemental analysis of Al, Si, and P was performed using Inductively Coupled Plasma (ICP) spectroscopy.

EXAMPLE 1

(Comparative) Synthesis of [Si—Al—P—O]-CHA with DMCHA

The following ingredients were mixed, in sequence, and blended into a uniform gel using a microhomogenizer (Tissue Tearor Model 98730, available from Biospec Products, Inc, USA): 85 wt % H₃PO₄ (obtained from Aldrich Chemical Company), deionized H₂O, Catapal™ A (73.9 wt % Al₂O₃, available from CONDEA Vista Company, Texas, USA), Cabosil™ (Cabot Company, USA), and then N,N-dimethyl-cyclohexylamine (DMCHA) (Aldrich Chemical Company, USA). The molar ratios of the ingredients were as follows:

1.5 DMCHA: 1.0 Al₂O₃: 1.0 P₂O₅: 0.1SiO2: 45 H₂O

The gel was heated in a sealed Teflon-lined Parr autoclave at 170° C. for 3 days while being tumbled at 40 rpm. The solid product was recovered and purified by centrifugation and washing with deionized water. The XRD of the powder product is given in FIG. 1 and indicated that the product was pure and had the CHA framework type.

EXAMPLE 2

(Comparative) Synthesis of SAPO-56 with TMHDA

The same ingredients and mixing sequence as in Example 1 were employed, except that N,N,N',N'-tetramethylhexane-1,6-diamine (TMHDA) (Aldrich) was added as template. The molar ratios of the gel composition were as follows:

1.5 TMHDA: 1.0 Al₂O₃: 1.0 P₂O₅: 0.45SiO2: 40 H₂O

The gel was heated with no agitation at 170° C. for 5 days followed by 200° C. for three days. The solid product similarly was recovered in Example 1, and was confirmed to be SAPO-56 as indicated by its XRD pattern (see FIG. 1).

EXAMPLE 3

Synthesis of AFX/CHA Intergrowths

The same ingredients and mixing sequence as in Example 1 were employed, except that both DMCHA and TMHDA were used as templates. Two gel compositions, Samples A and B, were produced and had the following molar ratios:

0.8 DMCHA: 1.1TMHDA: 1.0 Al₂O₃: 1.0 P₂O₅: 0.6SiO2: 40 H₂O for Sample A, 0.6 DMCHA: 1.2TMHDA: 1.0 Al₂O₃: 1.0 P₂O₅: 0.6SiO2: 40 H₂O for Sample B The gels were heated with no agitation at 180° C. for one day, followed by tumbling (40 rpm) at 180° C. for 10 days, and then without agitation again at 200° C. for three days. The XRD patterns of both Samples A and B are shown in FIG. 1.

Figure 1:
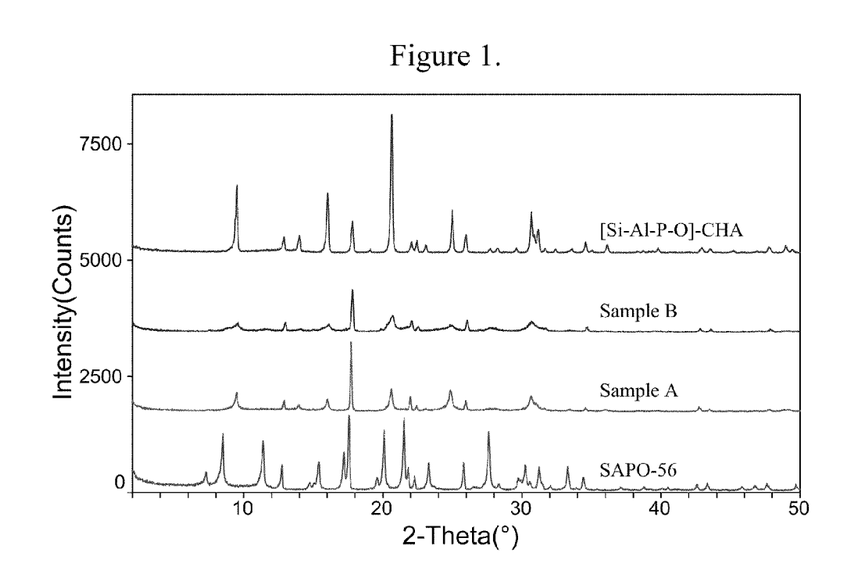
FIG. 1 gives the X-ray diffraction patterns of the products of Examples 1 and 2 and of Samples A and B of Example 3.

FIG. 1 shows that the XRDs of Samples A and B resemble that of [Si—Al—P—O]-CHA, not that of SAPO-56. The peak profile and intensities, however, are quite different from that of the [Si—Al—P—O]-CHA. Particularly noteworthy is the coexistence of sharp and broad peaks.

Figure 2:
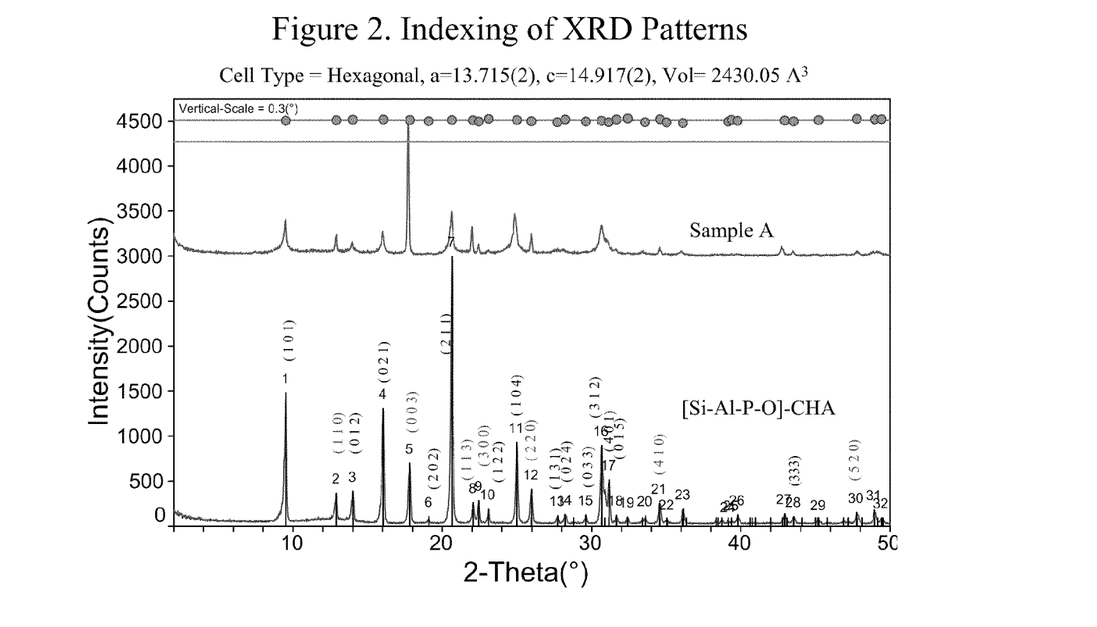
FIG. 2 indexes the X-ray diffraction pattern of Sample A of Example 3 against the X-ray diffraction pattern of a silicoaluminophosphate having the CHA framework type.

A closer inspection of the peaks of Sample A (same with Sample B, but not shown), with the entire pattern indexed [hexagonal unit cell, a=13.715(2), c=14.917(2)] and each reflection assigned with a respective Miller index, reveals that all reflections with (hk0) and (nn3) indices remain sharp, while all others are broadened (FIG. 2). This is entirely consistent with, and confirms, the disorderly stacking of D6R along the hexagonal axis according to the sequence of ABC (which yields the CHA framework) and occasionally ABCB (which yields the AFX framework), leading to a novel AFX/CHA intergrowth.

The following peak list shows peak intensity and peak width. It indicates, in numerical value, that sharp peaks (with FWHM<0.13, where FWHM is Full Width at Half Maximum, identified in italics) are those with either (hk0) or (nn3) indices. These Miller indices correspond to the crystal planes undisturbed by the intergrowth of hexagonal c-direction packing of AFX and CHA layers.

| (hkl) | 2θ | d (Å) | 100 × (I/I₀) | FWHM |
|---|---|---|---|---|
| 101 | 9.50 | 9.30 | 24 | 0.274 |
| *110* | *12.91* | *6.85* | *12* | *0.119* |
| 012 | 13.96 | 6.34 | 7 | 0.197 |
| 021 | 16.02 | 5.53 | 16 | 0.228 |
| *003* | *17.72* | *5.00* | *100* | *0.118* |
| 211 | 20.62 | 4.30 | 30 | 0.246 |
| *113* | *21.98* | *4.04* | *19* | *0.108* |
| *300* | *22.44* | *3.96* | *7* | *0.091* |
| 122 | 23.10 | 3.85 | 2 | 0.161 |
| 104 | 24.86 | 3.58 | 28 | 0.325 |
| *220* | *25.96* | *3.43* | *13* | *0.103* |

EXAMPLE 4

Effect of Template Ratio

Figure 3:
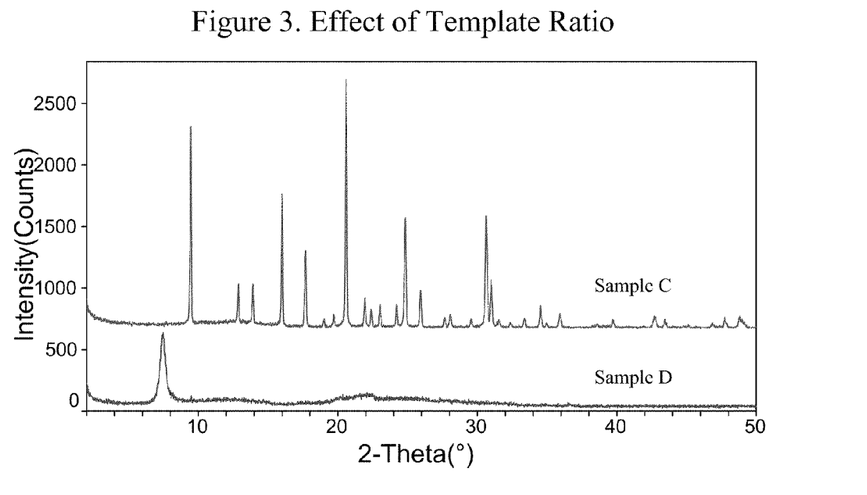
FIG. 3 gives the X-ray diffraction patterns of Samples C and D of Example 4.

The same ingredients and mixing sequence as in Example 3 were employed to produce two further gel compositions, Samples C and D, having the following molar ratios:

0.9 DMCHA: 1.05TMHDA: 1.0 Al₂O₃: 1.0 P₂O₅: 0.6SiO2: 40 H₂O for Sample C 0.5 DMCHA: 1.25TMHDA: 1.0 Al₂O₃: 1.0 P₂O₅: 0.6SiO2: 40 H₂O for Sample D For Sample C, the gel was heated while being tumbled at 180° C. for 18 days, and for Sample D the gel was heated while being tumbled at 175° C. for six days. The XRD patterns of both Samples C and D are shown in FIG. 3.

As expected, with more CHA template (DMCHA) in the gel, the product (Sample C) was [Si—Al—P—O]-CHA. When more AFX template (TMHDA) was used, the product was what appeared to be a layered phase, which had often been observed to form before the formation of SAPO-56 when only TMHDA was used as template. This example illustrates that the template ratio has an effect on whether AFX/CHA intergrowths form.

EXAMPLE 5

Effect of Agitation

The same ingredients and mixing sequence as in Example 3 were employed to produce an additional gel composition having the following molar ratios:

0.7 DMCHA: 1.15TMHDA: 1.0 Al₂O₃: 1.0 P₂O₅: 0.6SiO2: 40 H₂O

The gel was heated statically at 200° C. for three days. The XRD pattern of the product indicates that [Si—Al—P—O]-CHA had formed. This example showed that although the template ratio in this example was intermediate between those for Samples A and B of Example 1 (0.8 DMCHA: 1.1TMHDA and 0.6 DMCHA: 1.2TMHDA, respectively), no intergrowths formed, indicating that the AFX/CHA intergrowths form under well-controlled conditions in which agitation and/or staged heating appear to be important.

EXAMPLE 6

Summary of Composition and Adsorption Data

Data on elemental analysis and adsorption with n-hexane (at 90° C. and 90 torr), acetone (at 35° C. and 29.3 torr), and methanol (at 35° C. and 203 torr), along with preparation conditions for the samples in the above Examples 1 to 4 are shown in Table 1.

The data in Table 1 show that the AFX/CHA intergrowths have (1) higher n-hexane adsorption capacity than either [Si—Al—P—O]-CHA or SAPO-56; (2) much higher acetone adsorption capacity than [Si—Al—P—O]-CHA, especially more than SAPO-56 (by 76%); and (3) comparable methanol adsorption capacity.

EXAMPLE 7

MTO Performance of AFX/CHA Intergrowths (a) Table 2 summarizes MTO testing conditions and results on the two intergrowth Samples A and B. The results show that the materials are active for methanol conversion to light olefins, but exhibit lower light olefin selectivity and higher selectivity for light saturates and coke than typical SAPO-34 catalysts.

(b) While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of synthesizing a molecular sieve comprising at least one intergrown phase of an AFX framework-type molecular sieve inserted along the hexagonal axis into at least one intergrown phase of a CHA framework-type molecular sieve, the method comprising:
   (a) preparing a reaction mixture comprising sources of alumina, phosphorus, and, optionally, silica and further comprising at least one first organic directing agent for directing the synthesis of an AFX framework-type molecular sieve and at least one second organic directing agent for directing the synthesis of a CHA framework-type molecular sieve;
   (b) maintaining said reaction mixture under conditions sufficient to form crystals of said molecular sieve; and
   (c) recovering said molecular sieve comprising at least one intergrown phase of an AFX framework-type molecular sieve inserted along the hexagonal axis into at least one intergrown phase of a CHA framework-type molecular sieve.

2. The method of claim 1, wherein said at least one first organic directing agent comprises N,N,N'N'-tetramethylhexane-1,6-diamine.

3. The method of claim 1, wherein said at least one second organic directing agent comprises N,N-dimethylcyclohexylamine.

4. The method of claim 1, wherein said reaction mixture in (a) has a molar composition within the following ranges:
   $P_2O_5:Al_2O_3$ from about 0.75 to about 0.25,
   $SiO_2:Al_2O_3$ from about 0.1 to about 0.8, and
   $H_2O:Al_2O_3$ from about 25 to about 80.

5. The method of claim 1, wherein said reaction mixture in (a) has a silica to alumina molar ratio of at least 0.2.

6. The method of claim 1, wherein the conditions in (b) include a temperature between about 120° C. and about 220° C. for a period of time of from about 12 to about 480 hours.

7. The method of claim 1, wherein the conditions in (b) include a temperature between about 140° C. and about 200° C. for a period of time of from about 24 to 360 hours.

8. The method of claim 1, wherein (b) is conducted in a least first and second crystallization stages.

9. The method of claim 8, wherein the first crystallization stage includes a first temperature in the range of about 150° C. to about 200° C. for a first period of time from about 24 to about 360 hours.

10. The method of claim 9, wherein the second crystallization stage includes a second temperature higher than the first temperature and in the range of about 170° C. to about 220° C. for a second period of time from about 24 to about 96 hours.

11. The method of claim 8, wherein the reaction mixture is agitated during one or both of the first and second crystallization stages.

TABLE 1

| Example/ Sample | Synthesis Conditions ||||||| | Adsorption, Wt % |||  |
|---|---|---|---|---|---|---|---|---|---|---|---|---|
|  | Gel Composition, Ratio to $Al_2O_3$ ||| Heating 1 || Heating 2 || Product | n-Hexane Uptake, Wt % 90° C., 90 Torr | Acetone Uptake, Wt % 35° C., 29.3 Torr | MeOH Uptake, Wt % 35° C., 203 Torr | Phase |
|  | DMCHA | TMHDA | $SiO_2$ | T, ° C. | t, day | T, ° C. | t, day | Composition |  |  |  |  |
| 1 | 1.50 | 0.00 | 0.10 | 170 | 3 | NA | NA | $Si_{0.063}Al_{1.0}P_{0.952}$ | 11.3 | 18.9 | 24.5 | CHA |
| 2 | 0.00 | 1.50 | 0.45 | 170 | 5 | 200 | 3 | $Si_{0.309}Al_{1.0}P_{0.737}$ | 10.7 | 13.8 | 22.3 | AFX |
| 3A | 0.80 | 1.10 | 0.60 | 180 | 10 | 200 | 3 | $Si_{0.347}Al_{1.0}P_{0.731}$ | 12.7 | 24.4 | 22.8 | Intergrowth |
| 3B | 0.60 | 1.20 | 0.60 | 180 | 10 | 200 | 3 | $Si_{0.352}Al_{1.0}P_{0.722}$ | 13.5 | 24.8 | 23.0 | Intergrowth |
| 4C | 0.90 | 1.05 | 0.60 | 180 | 14 | NA | NA | $Si_{0.333}Al_{1.0}P_{0.763}$ | — | — | — | CHA |
| 4D | 0.50 | 1.25 | 0.30 | 175 | 6 | NA | NA | — | — | — | — | Layered |

TABLE 2

| Sample | T, ° C. | Pressure (psig) | WHSV (sieve) | Total g. MeOH converted | Initial Conv. | CH4 | C2= | C2o | C3= | C3o | C4= | C4o | C4= | C5+ | Coke |
|---|---|---|---|---|---|---|---|---|---|---|---|---|---|---|---|
| A | 475 | 25.4 | 100 | 3.6 | 99.7 | 2.2 | 25.6 | 2.1 | 31.5 | 9.2 | 15.2 | 0.0 | 15.2 | 4.1 | 9.7 |
| B | 475 | 25.2 | 100 | 2.9 | 99.7 | 2.8 | 26.5 | 2.1 | 30.8 | 9.2 | 13.9 | 0.0 | 13.9 | 3.4 | 10.9 |

12. The method of claim 8, wherein the reaction mixture is agitated during the first crystallization stage and held static during the second crystallization stage.

13. An organic compound conversion process comprising contacting an organic compound under conversion conditions with a catalyst comprising a molecular sieve comprising at least one intergrown phase of an AFX framework-type molecular sieve inserted along the hexagonal axis into at least one intergrown phase of a CHA framework-type molecular sieve.

14. The organic compound conversion process of claim 13, wherein the molecular sieve is a silicoaluminophosphate molecular sieve.

15. The organic compound conversion process of claim 13, wherein the AFX framework-type is present in the at least one intergrown phase of the molecular sieve in a proportion to the CHA framework-type from about 5% to about 95%.

16. The organic compound conversion process of claim 13, wherein the molecular sieve comprises from about 1 wt % to about 99 wt % of the at least one intergrowth and from about 99 wt % to about 1 wt % of a second molecular sieve.

17. The process of claim 13, wherein said organic compound comprises an organic oxygenate compound and the conversion process converts said organic oxygenate compound to a product comprising olefins.

18. The process of claim 17, wherein said organic oxygenate compound comprises methanol, dimethyl ether, or a mixture thereof, and said olefins comprise ethylene and propylene.

* * * * *